US010016252B1

(12) United States Patent
Wren, Sr.

(10) Patent No.: US 10,016,252 B1
(45) Date of Patent: Jul. 10, 2018

(54) SURGERY PATIENT ENCAPSULATING STERILE BUBBLE

(71) Applicant: Peter Wren, Sr., Birmingham, AL (US)

(72) Inventor: Peter Wren, Sr., Birmingham, AL (US)

(*) Notice: Subject to any disclaimer, the term of this patent is extended or adjusted under 35 U.S.C. 154(b) by 0 days.

(21) Appl. No.: 15/686,470

(22) Filed: Aug. 25, 2017

Related U.S. Application Data

(63) Continuation-in-part of application No. 15/336,987, filed on Oct. 28, 2016, now abandoned.

(51) Int. Cl.
| A61B 90/40 | (2016.01) |
| A61G 10/02 | (2006.01) |
| A61G 10/00 | (2006.01) |
| A61B 90/57 | (2016.01) |
| A61B 42/10 | (2016.01) |
| A61B 18/22 | (2006.01) |
| A61B 90/50 | (2016.01) |
| A61G 13/10 | (2006.01) |
| A61G 10/04 | (2006.01) |
| A61M 16/06 | (2006.01) |

(52) U.S. Cl.
CPC .............. *A61B 90/40* (2016.02); *A61B 18/22* (2013.01); *A61B 42/10* (2016.02); *A61B 90/50* (2016.02); *A61B 90/57* (2016.02); *A61G 10/005* (2013.01); *A61G 13/108* (2013.01); A61B 2018/225 (2013.01); A61B 2090/401 (2016.02); A61B 2090/506 (2016.02); A61G 10/04 (2013.01); A61G 2203/30 (2013.01); A61M 16/06 (2013.01); A61M 16/0672 (2014.02)

(58) Field of Classification Search
CPC ....... A61G 10/00–10/04; A61G 13/108; A61B 90/40; A61B 90/57; A61B 2090/401
See application file for complete search history.

(56) References Cited

U.S. PATENT DOCUMENTS

| 3,858,570 | A | 1/1975 | Beld et al. |
| 4,089,571 | A | 5/1978 | Landy |
| 4,945,924 | A | 8/1990 | Poettgen |
| 5,074,894 | A | 12/1991 | Nelson |
| 5,292,347 | A | 3/1994 | Pompei |
| 5,503,143 | A | 4/1996 | Marion et al. |
| 5,728,041 | A | 3/1998 | Fowler, Jr. |
| 5,800,483 | A | 9/1998 | Vought |
| 6,016,803 | A | 1/2000 | Volberg et al. |
| 6,500,199 | B1 | 12/2002 | Becker et al. |
| 6,899,103 | B1 | 5/2005 | Hood et al. |
| 6,966,937 | B2 | 11/2005 | Yachi et al. |
| 7,108,713 | B1 | 9/2006 | Augustine |
| 2002/0045796 | A1* | 4/2002 | O'Connor ............. A61B 90/40 600/21 |

(Continued)

FOREIGN PATENT DOCUMENTS

EP    0619108 A1    3/1994

Primary Examiner — Thaddeus Cox
(74) Attorney, Agent, or Firm — George L Williamson

(57) ABSTRACT

A system and method for providing a surgery table or bed adapted to encapsulate a patient to provide a sterile environment during surgery. The apparatus is configured to include an enclosure that is filled with an inert and sterile gas prior to surgery. The patient is accessed through internally extending gloves for use by the surgical staff.

15 Claims, 2 Drawing Sheets

(56) References Cited

U.S. PATENT DOCUMENTS

2003/0129938 A1\* 7/2003 Mitchell ................ A61G 10/00
                                                    454/187
2014/0316455 A1\* 10/2014 Gnanashanmugam ....................
                                                    A61B 19/38
                                                    606/202

\* cited by examiner

SURGERY PATIENT ENCAPSULATING STERILE BUBBLE

BACKGROUND OF THE INVENTION

Field of the Invention

The present invention relates generally to the field of medical accessories and, more particularly, is concerned with a device for enclosing and thereby isolating a patient during a surgical procedure wherein the patient may have cancer or be suspected of having such a disease.

While surgery is usually the last option that is considered to treat many types of illnesses, diseases, or deficiencies, it still results in a high rate of recovery, and an improvement in the patient's general health. Besides the actual surgical procedure itself, a great deal of the processes used in any type of surgery are there to prevent infection. Not only must all instruments, tools, and devices be sterilized, but the air in the room itself must be clean as well. Even after using complex ventilation systems with high efficiency filters, dual door locks, and the like, germs, bacteria, and other contaminants can still be in the air, and make contact with the patient. When one factors in the patient's reduced level of immunity, infection, disease, and even worse is often the result. Accordingly, there exists a need for a means by which surgery patients can be protected from air-borne contaminants. The development of the present invention fulfills this need.

Description of the Related Art

Devices relevant to the present invention have been described in the related art, however, none of the related art devices disclose the unique features of the present invention.

In European Patent Application EP0619108A1 dated Mar. 24, 1994, Uri, et al., disclosed a device for isolating a patient. In U.S. Pat. No. 4,945,924 dated Aug. 7, 1990, Poettgen disclosed a sterilizable, reflective surgical drape. In U.S. Pat. No. 5,074,894 dated Dec. 24, 1991, Nelson disclosed an apparatus for isolating contagious, respiratory hospital patients. In U.S. Pat. No. 5,292,347 dated Mar. 8, 1994, Pompei disclosed a method and apparatus for regulating body temperature. In U.S. Pat. No. 5,800,483 dated Sep. 1, 1998, Vought disclosed a system and method for sterile, surgical thermal drape with active air circulation. In U.S. Pat. No. 6,500,199 dated Dec. 31, 2002, Becker, et al., disclosed an enclosure bag for maintaining a patient's body temperature during surgical procedures. In U.S. Pat. No. 6,966,937 dated Nov. 2, 2005, Yachi, et al., disclosed a patient isolation unit. In U.S. Pat. No. 7,108,713 dated Sep. 19, 2006, Augustine disclosed a surgical barrier device incorporating an inflatable, thermal blanket with a surgical drape to provide thermal control and surgical access. In U.S. Pat. No. 6,899,103 dated May 31, 2005, Hood, et al., disclosed a self contained transportable life support system. In U.S. Pat. No. 4,089,571 dated May 16, 1978, Landy disclosed a glove port and insert. In U.S. Pat. No. 3,858,570 dated Jan. 7, 1975, Beld, et al., disclosed a comprehensive infant care system. In U.S. Pat. No. 5,728,041 dated Mar. 17, 1998, Fowler, Jr., disclosed an isolator for use in surgery or as a clean room and method of using the same.

While these devices may be suitable for the purposes for which they were designed, they would not be as suitable for the purposes of the present invention as hereinafter described. As will be shown by way of explanation and drawings, the present invention works in a novel manner and differently from the related art.

SUMMARY OF THE PRESENT INVENTION

The present invention discloses a system for providing a sterile environment for a patient during surgery which includes a clear, generally rectangular domed shaped enclosure within which the patient is enclosed. While the overall size of the invention can vary per patient size, it is envisioned that a typical size would be about three feet high, three feet wide, and seven feet long being sized for a typical adult patient. A plurality of access points with sealed rubber gloves are provided on all surfaces of the enclosure. A plurality of sealed access ports are provided to allow for medications, paraphernalia for transfusions, air lines, and the like to be placed inside the enclosure. Likewise, a plurality of ports for removal of items such as vacuum lines, dual sealed sample ports, and the like are also provided. The present invention also provides access for monitoring sensors, display monitors and the like. The necessary surgical tools would also be placed inside the enclosure with the patient before surgery begins. In operation, the enclosure would be purged with sterile gas prior to surgery, and remain under positive pressure to avoid the entrance of any ambient outside air which could cause infection.

An object of the present invention is to provide an environment for surgery in a manner that is quick, easy and effective, and results in decreased chances of infection along with increased quality of care for the patient as well. An object of the present invention is to provide a sterile enclosure within which surgery can be safety conducted. An object of the present invention is to provide a sterile environment for use with all types of surgery including surgery related to cancer. A further object of the present invention is to provide an enclosure having a positive pressure therein to prevent the entry of contaminants. A further object of the present invention is to provide a sterile surgical environment which can be easily operated by a user. A further object of the present invention is to provide a sterile surgical environment which can be relatively easily and inexpensively manufactured.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

LIST OF REFERENCE NUMERALS

Figure 1:
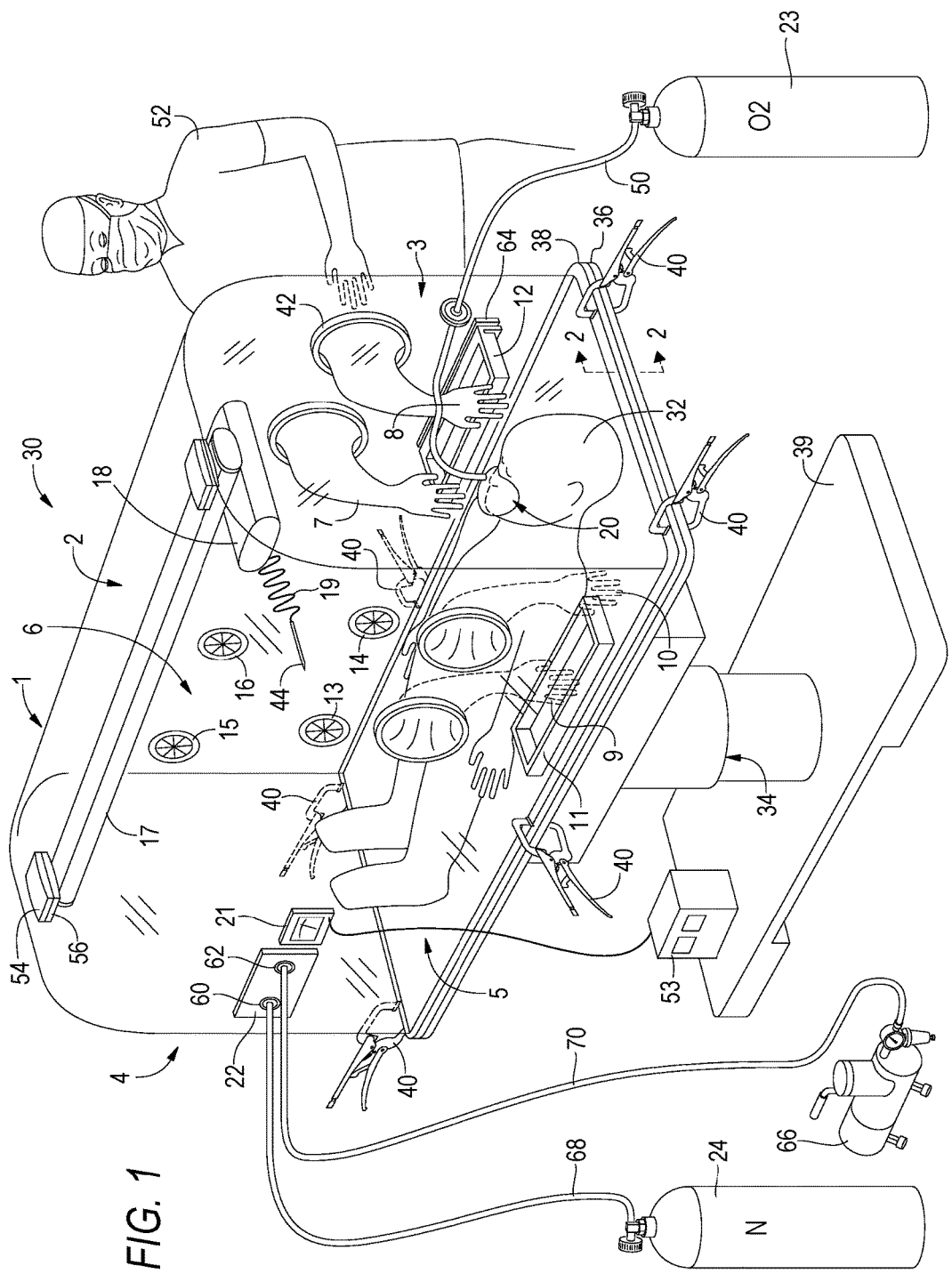
FIG. 1 is a perspective view of the present invention in operative connection.

With regard to reference numerals used, the following numbering is used throughout the drawings.
1 enclosure
2 top of enclosure
3 front of enclosure
4 back of enclosure
5 left side
6 right side
7 surgical gloves
8 surgical gloves
9 surgical gloves
10 surgical gloves
11 surgical tray
12 surgical tray
13 junction receptacles
14 junction receptacles
15 junction receptacles
16 junction receptacles
17 laser rack
18 guide for mobile compartment
19 laser coil
20 breathing mask
21 oxygen analyzer
22 junction connector
23 oxygen canister
24 nitrogen canister
25 rubber gasket
30 present invention
32 patient
34 operating table
36 upper planar portion of operating table
38 lip of enclosure
39 support base of operating table
40 clamp
42 seals for gloves
44 handpiece
48 gasket
50 breathing tube
52 surgeon
53 oxygen regulator
54 outer mounting bracket
56 inner mounting bracket
58 flexible flap portion
60 input port
62 output port
64 mount
66 vacuum pump
68 conduit
70 conduit

DETAILED DESCRIPTION OF THE PREFERRED EMBODIMENT

The following discussion describes in detail at least one embodiment of the present invention. This discussion should not be construed, however, as limiting the present invention to the particular embodiments described herein since practitioners skilled in the art will recognize numerous other embodiments as well. For a definition of the complete scope of the invention the reader is directed to the appended claims. FIGS. 1 through 5 illustrate the present invention wherein a system for a sterile surgical enclosure for encapsulating a patient is disclosed and which is generally indicated by reference number 30.

Figure 2:
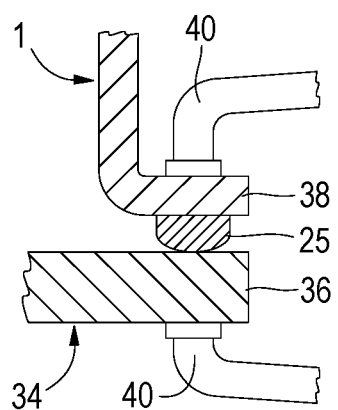
FIG. 2 is cross-sectional view taken from FIG. 1 as indicated.

Turning to FIG. 1, therein is shown enclosure 1 as being made of a pliable, transparent plastic material approximately ½" thick and weighing approximately 25 pounds. It has a front 3, back 4, left side 5, right side 6 and top 2. The enclosure 1 is about seven feet (7') in length, three feet (3') wide and three feet (3') high with a 1½" lip 38 along its lower edge specifically designed so that clamping it to a standard operating table 34 with clamp 40 is simple and secure. Enclosure 1, being somewhat bubble shaped, is designed to be disposed onto the upper surface 36 of any conventional surgical/operating table 34 having the ability to accommodate any human patient or subject 32 of average size. The bottom portion of the enclosure 1 is sealed to the upper surface 36 of the operating table with a rubber gasket 25 as best shown in FIG. 2 so as to provide an airtight seal between the enclosure and the operating table. Operating table 34 has an upper flat surface 36 to which the enclosure 1 is attached and a supporting base 39 for placement on a supporting surface such as a floor.

On the left 5 and right 6 sides there may be necessary instruments attached for successful monitoring of the enclosed subject or patient 32. The enclosure 1 is made of lightweight plastic so that it is easy to maneuver and economical to produce. While the term "patient", indicated by reference numeral 32, may be used in this specification, it is not the intent of the inventor to attempt to invent, claim or patent a human organism or human body rather a sterile surgical enclosure for encapsulating one undergoing a surgical procedure. Other terms which may be used instead of a patient include a medical patient, a subject, an object, a thing, a one, or, one that is being discussed, described, or dealt with or which is undergoing a surgical procedure in the sterile surgical enclosure 1 of the present invention 30.

Enclosure 1 minimizes the amount of oxygen that is allowed to enter the enclosure during the surgical process and thereby eliminates the possibility of the spread of the cancer cells. All necessary tools and monitors are strategically placed inside the enclosure 1 prior to the surgical procedure and the oxygen level is brought to near zero.

There is an oxygen analyzer 21 attached to the left side 5 of the enclosure 1 so that the oxygen analyzer probe can monitor the level of oxygen present in the enclosure; an oxygen regulator is shown at 53. The presence of oxygen should be minimal to near zero inside the enclosure 1. The input of nitrogen into the enclosure 1 is through the junction connector 22 from the nitrogen canister 24 outside the enclosure through a 2" transfer tube/conduit 68. Junction connector 22 includes input port 60 and output port 62. The oxygen analyzer 21 will allow the flow of nitrogen from the nitrogen canister 24 into the enclosure to be monitored to ensure the gasses are kept at an acceptable level inside the enclosure at all times. When the oxygen level approaches zero it can be assumed that the nitrogen level is sufficiently high. It should be understood that oxygen levels less than about ten percent are considered low. It is expected that the present invention 30 will provide oxygen levels inside the enclosure 1 of less than one percent (1%), and, alternatively, may approach substantially zero oxygen. To assist in obtaining and maintaining such oxygen levels an effectively sized vacuum pumping system is provided including a vacuum pump 66 which is connected to the enclosure 1 through conduit 70 using output port 62 of junction connector 22. Vacuum pump 66 assists in evacuating oxygen from inside the enclosure 1 so that the oxygen may be replaced with nitrogen. Alternatively, the vacuum pump 66 may connected directly to enclosure 1.

The front of the enclosure 1 has an access point or port allowing oxygen to be filtered into the patient 32 through the breathing mask 20. The breathing mask 20 is about 4" high and 3" wide and attached to a 2" in diameter and a six foot (6' long) breathing tube to the oxygen canister 23 outside of the enclosure 1. This oxygen is being sent into the patient 32 through mask 20 to ensure the necessary amount of oxygen is continually supplied to the patient during the surgical procedure.

On the left 5 and right 6 sides of the enclosure 1 are a set of pressurized seals 42 that allow for disposable surgical gloves 7, 8, 9, and 10 that are about 3' in length to be attached and used by medical personnel, e.g., a surgeon 52, performing the procedures. The gloves 7-10 are to be disposed of after each completed procedure.

There are also on the left 5 and right 6 sides of the enclosure 1, junction receptacles or sealed gaskets 13, 14, 15, 16 that are about 3" in diameter placed between or near the junction connector 22 and the disposable gloves 7, 8, 9, 10 through which to administer needed medicines and remove surgical tools that have served the purpose for this particular procedure. These sealed gaskets 13-16 are airlock fit to eliminate the movement of air into or from the enclosure 1 during surgical procedures.

The top portions 2 of the enclosure 1 has an attachment mounted as the laser rack 17, which is the guide for the mobile compartment 18 which houses the laser coil 19 and handpiece 44 used to perform the actual surgical procedure. The laser rack 17 extends about the length of the enclosure 1 which allows the laser to be moved to any portion of the body of the patient 32. Outer mounting bracket 54 is shown on the outside of enclosure 1 to which is attached inner mounting bracket 56 for mounting laser rack 17 to the enclosure in the standard manner as would be done by one skilled in the art.

On the left 5 and right 6 sides of the enclosure 1 are surgical trays 11, 12 made of stainless steel. These steel trays 11, 12 are for placement therein of all surgical tools necessary in the procedure and are to be placed inside the enclosure 1 before the air is sterilized for surgery and oxygen levels are brought to near zero. Tray 12 is attached to the inner surface of enclosure 1 using mount 64 while tray 11 rests on the surface 36 of operating table 34.

All parts that are used during the surgery are disposable and, therefore, disposed of after each procedure which serves to limit the amount of decontamination procedures necessary that need to take place after each procedure.

Figure 3:
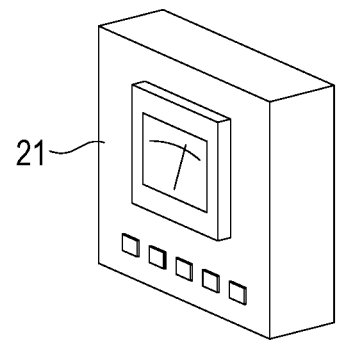
FIG. 3 is a perspective view of portions of the present invention.
Figure 4:
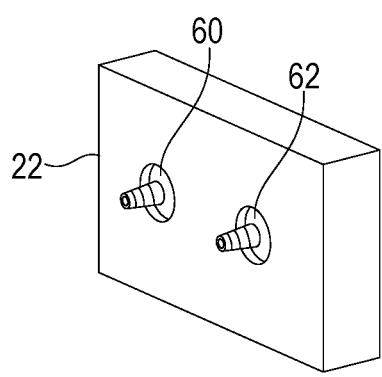
FIG. 4 is a perspective view of portions of the present invention.
Figure 5:
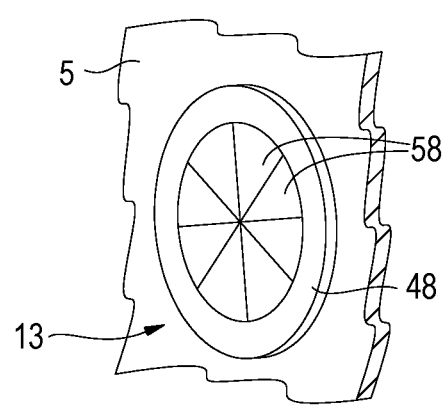
FIG. 5 is a perspective view of portions of the present invention.

Turning to FIG. 2, therein is shown a gasket 25 between the lip 38 of the enclosure 1 and the operating table 36 being held together with clamp 40 as previously described. Turning to FIG. 3, therein is shown the oxygen analyzer 21. Turning to FIG. 4, therein is shown the junction connector 22 having an input port 60 and an output port 62 for the connection of tubes or conduits as would be done in the standard manner by one skilled in the art. Turning to FIG. 5, therein is shown the junction receptacle 13 having a plurality of triangular-shaped flexible flap portions 58 and being sealed to the enclosure 5 using a gasket 48 or the like as would be done in the standard manner by one skilled in the art. Receptacle 13 provides an access port into the enclosure 1 by having the rubber-like flap portion 58 flex to allow a user to insert a hand into the enclosure and after withdrawal of the hand the flap will return to its original shape so as to reclose the access port.

The following additional discussion makes reference to the present invention 30 and to FIGS. 1-5.

The present invention 30 has an enclosure 1 for isolating a patient 32 made of clear, transparent, shatterproof material, e.g., PLEXIGLASS. The material is clearer than glass, so where glass reaches thickness limitations as a window fairly low, it can have thicknesses up to 13 inches. This feature makes the material ideal for aquariums having relatively high internal pressure wherein it can be thick enough to hold back thousands of gallons of water without blurring or distorting the view from the outside. It is also the same material used around ice rinks where hockey games are held, preventing pucks from flying into the crowd.

Acrylic plastic refers to a family of synthetic, or man-made, plastic materials containing one or more derivatives of acrylic acid. The most common acrylic plastic is polymethyl methacrylate (PMMA), which is sold under the brand names of PLEXIGLAS, LUCITE, PERSPEX and CRYSTALLITE. PMMA is a tough, highly transparent material with excellent resistance to ultraviolet radiation and weathering. It can be colored, molded, cut, drilled and formed. These properties make it ideal for many applications including the present invention 30. Because the acrylic plastic is able to be manipulated it is less fragile than glass and, therefore, more durable. The enclosure 1 of the present invention 30 is expected to be made of about ½" PLEXIGLAS or the like; also, the enclosure is expected to be curved at the top 2 so as to assist in forming a more secure enclosure.

The enclosure 1 has a front 3, back 4, left 5, right 6 and top 2. The enclosure 1 is designed to fit over the top of a standard adult person/patient 32; the bottom portion of the enclosure is trimmed with 1" thick rubber gasket 25 material or the like. The natural rubber, also called India rubber or caoutchouc, as initially produced, consists of polymers of the organic compound isoprene, with minor impurities of other organic compounds plus water. Malaysia is a leading producer of rubber. Forms of polyisoprene that are used as natural rubbers are classified as elastomers. Natural rubber is used by many manufacturing companies for the production of rubber products. Currently, rubber is harvested mainly in the form of the latex from certain trees. The latex is a sticky, milky colloid drawn off by making incisions into the bark and collecting the fluid in vessels in a process called "tapping." The latex is then refined into rubber ready for commercial processing. Natural rubber is used extensively in many applications and products, either alone or in combination with other materials. In most of its useful forms, it has a large stretch ration and high resilience, and is extremely waterproof. Each of the four corners of the enclosure 1 of the present invention 30 has about a 1½" lip designed specifically to be clamped, using clamps 40, to the upper planar portion 36 surgical table 34 thereby creating an airtight seal between the lower edge of the enclosure and the surgical table 34.

Clamps 40 are a versatile part of any tool kit; they can be used to secure a workpiece to a work surface, to secure a straight edge across a work area for procedures, or to hold pieces of a machine securely. The present invention 30 uses a clamp 40 which is an instrument used to compress or hold in place a bodily structure at each of the four corners. These clamps 40 are a vital part of any project, as they ensure stability and security to the entity they hold.

An oxygen analyzer 21 is connected to a probe on the left side of the enclosure 1 in order to measure the level of oxygen present in the enclosure 1 at all times. This system provides a real-time reading to ensure there is near zero oxygen in the enclosure 1 during surgical procedures. The oxygen analyzer 21 is perfect for facilities using nitrogen, helium and argon and is also suited for use in confined spaces, cryogenic facilities and freezers. The monitor 21 remains accurate at temperatures as low as −40 degrees Centigrade. The monitor 21 measures the internal atmosphere to ensure the correct levels of oxygen are maintained inside the enclosure 1 during surgery.

On the left side 5 of enclosure 1, there is also the junction connector 22 which is for nitrogen input to provide nitrogen into the enclosure 1 to assist in lowering the oxygen levels. These junction connectors 22 can be single or multiport.

A nitrogen canister 24 is used to suppress the presence of oxygen inside the enclosure 1 to a level of near zero until the procedure is complete. Nitrogen is substantially an inert, non-reactive gas. It has no color, odor or taste. Nitrogen is also present in every living thing on the planet. The earth's atmosphere is almost 80% nitrogen; however, it is pure gas form it cannot be used by living organisms.

Because atmospheric nitrogen gas is unstable for all organisms, some bacteria have evolved the ability to add hydrogen atoms to nitrogen and create ammonia, therefore, the monitors 21 will ensure the levels are kept at a safe level internal the enclosure 1 during surgical procedures.

On either side of the enclosure 1 are junction receptacles 13-16 which are strategically placed for the input/insertion (hence the name junction receptacle as in receiving) or removal of necessary medicines or surgical tools, such as medications, transfusions, air lines and the like. The ports or receptacles 13-16 will minimize fluctuations of temperature and carbon dioxide during activity. The small, sealed gaskets 48 around the outer edges of the junction receptacles 13-16 are tightly fit to the enclosure 1 to minimize the chance of changing the oxygen level in the enclosure during surgical procedures.

Also located on both left and right sides of the enclosure 1 are surgical trays 11-12 which are used to carry surgical instruments and are rectangular and made of stainless steel to resist the heat of sterilization without corrosion. A tray is a shallow platform designed for carrying things. It can be fashioned from numerous materials, including silver, brass, sheet iron, paperboard, wood, melamine and molded pulp. Trays range in cost from inexpensive, molded pulp trays which are disposable, to inexpensive silver trays used in luxury hotels. Some examples have raised galleries, handles and short feet for support. The trays are flat but with raised edges to stop items from sliding off. They are made in a range of shapes, but are commonly found in oval or rectangular forms, sometimes with cutout or attached handled to be used for carrying.

On the left and right sides of the enclosure 1 are pressurized inserts in the form of surgical gloves 7-10 which are disposable gloves used during medical examinations and procedures that help prevent cross-contamination between caregivers and patients. Gaskets 42 are provided around a circular base of the gloves 7-10 to provide an airtight seal between the base and enclosure 1. Medical gloves are made of different polymers including latex, nitrile rubber, vinyl and neoprene. They come in un-powdered, or powdered with cornstarch to lubricate the gloves, making them easier to put on the hands. Cornstarch replaced tissue-irritating Lycopodium powder and talc, but even cornstarch can impede healing if it gets into tissues (as during surgery). As such, un-powdered gloves are used more often during surgery and other sensitive procedures. Special manufacturing processes are used to compensate for the lack of powder. There are two main types of medical gloves: examination and surgical. Surgical gloves have more precise sizing with a better precision and sensitivity and are made to a higher standard. Examination gloves are available as either sterile or non-sterile while surgical gloves are generally sterile.

Laser surgery is surgery using a laser (instead of a scalpel) to cut tissues. Examples include the use of a laser scalpel in otherwise conventional surgery, and soft-tissue laser surgery, in which the laser beam vaporizes soft tissue having high water content. The term laser means light amplification by simulated emission of radiation, and it uses a laser light source (laser beam) to remove tissues that are diseased or to treat blood vessels that are bleeding. Laser beams are strong beams of light produced by electrically stimulating a particular material. A solid, liquid, or a gas is used. Alternatively, the laser is used cosmetically; it can remove wrinkles, birthmarks or tattoos.

According to the surgical encyclopedia, the special light beam is focused to treat tissues by heating the cells until they burst. There are a number of different laser types. Each has a different use and color. The color, or the light beam, relates to the type of surgery that is being performed and the color of the tissue that is being treated. There are three types of laser: the carbon dioxide (CO2) laser, the YAG laser (yttrium aluminum garnet); and the pulsed dye laser.

Laser surgery is used to (a) cut or destroy tissue that is abnormal or diseased without harming health, normal tissue; (b) shrink or destroy tumors and lesions; (c) close off nerve endings to reduce postoperative pain; (d) cauterize (seal) blood vessels to reduce blood loss; (e) seal lymph vessels to minimize swelling and decrease spread of tumor cells; (f) remove moles, warts, and tattoos, and, (g) decrease the appearance of skin wrinkles.

The top of the enclosure 1 houses the laser rack 17 which has a length about the length of the enclosure and the home of the mobile compartment that holds the laser coil 19 having a handpiece 44 thereon. The laser coil 19 is a device that transfers light of various frequencies into an extremely intense, small, and nearly non-divergent beam of monochromatic radiation in the visible or invisible spectrum, with all the waves in phase; capable of mobilizing immense heat and power when focused at close range. Lasers act on tissues by photocoagulation and photo disruption and may be used during surgery in this enclosure 1. The coil 19 allows for great mobility for the surgeon to move the laser along the full length of the patient while the patient remains encapsulated without breaking the seal of enclosure 1. Research shows all live human cells can be killed almost immediately at severely elevated temperatures (above 57 degrees C.) through various processes, including protein denaturation, coagulation and vaporization. At lower temperatures (43 degrees-57 degrees C.) tissular necrosis (tissue death due to protein denaturation) will occur with exposure from minutes to hours. Use of the attached laser coils 19 focuses on areas of surgical interest and can be minimally invasive.

The use of a low power laser with a specialized probe can heat and coagulate a tumor from within. An advantage of laser usage compared to externally applied energy is that the energy is applied directly to the area of interest rather than passing through surrounding normal tissue.

The front of the enclosure 1 has an opening for the breathing apparatus to be placed on the patient 32 and be monitored in the form of a breathing mask 20 for oxygen intake. The mask 20 is about 4" high and 3" wide connected to a 6' tube which is 2" in diameter. The mask 20 must be airtight over the patient's face so as to not seep oxygen into the enclosure 1 during the surgical procedure. All measurements are approximate.

A breathing tube is a flexible tube for breathing through, as part of a scuba set or other breathing apparatus or a medical oxygen apparatus or anesthetic apparatus. (Here they are distinguished from the medium-pressure hoses which are often found as parts of modem breathing apparatus.) They are wide and usually corrugated to let the user's head move about without the tube pinching at kinks. Each end of the tubing usually has a screw connection. They may contain a one-way valve to keep the air or gas flowing in the right direction.

Breathing tube 50 has to be long enough to connect the oxygen canister 23 to the patient's breathing mask 20, but should not loop about excessively to cause hydrodynamic drag or risk snagging or contain excess dead space.

The oxygen canister 23 is placed on the outside of the enclosure 1 to be used so as to ensure the patient 32 maintains an adequate level of oxygen in the body during the entire time of the procedure. The oxygen will be administered through the flexible breathing tube 50 which is about 6' in length and 2" in diameter as previously mentioned.

All dimensions and weights presented in this specification are approximate in value.

I claim:

1. A system for enclosing a subject on an operating table during a surgical procedure for removal of a suspected cancer, the subject wearing a breathing mask and configured to be positioned on an upper surface of the operating table, comprising:
   a) a transparent enclosure having a lower lip extending completely around a periphery of said enclosure, and mounted over said operating table having an upper planar portion extending to an outer edge thereof, a gasket between said lower lip and said outer edge of said upper planar portion extending completely around said enclosure, and clamps engaging said lower lip and said outer edge of said upper planar portion for sealing said enclosure to said upper surface of said operating table to provide an airtight seal between said enclosure and said operating table, said enclosure containing surgical trays for carrying surgical instruments for performing said surgical procedure;
   b) a plurality of surgical gloves disposed on an interior surface of said enclosure, wherein medical personnel can insert their hands into said surgical gloves to permit the medical personnel to perform the surgical procedure while the medical personnel are positioned outside of said enclosure, and junction receptacles mounted in a wall of said enclosure for administering needed medicines;
   c) a source of oxygen, said source of oxygen adapted to supply oxygen directly to said breathing mask during the surgical procedure;
   d) apparatus for maintaining an atmosphere containing oxygen which is less than 1% of said oxygen under positive pressure within said enclosure outside of said breathing mask comprising a source of inert gas absent any oxygen for supplying said inert gas to an interior of said enclosure in sufficient amounts, as determined by an oxygen analyzer within said enclosure, to displace air within said enclosure and obtain and maintain said atmosphere of said inert gas with oxygen level brought to less than 1% within said enclosure during said surgical procedure in order to eliminate any possibility of spread of cancer cells;
   e) wherein said air is purged from said enclosure by said inert gas; and
   f) a laser adapted to perform said surgical procedure movably mounted on a rack fixed on the interior of said enclosure for performing laser surgery inside said enclosure in an environment of less than 1% oxygen.

2. The system of claim 1, further comprising a plurality of access ports being disposed in said enclosure to permit articles to be passed from the outside of said enclosure to the interior of said enclosure.

3. The system of claim 2, wherein said plurality of surgical gloves are adapted to form an airtight seal between said enclosure and said plurality of surgical gloves.

4. The system of claim 3, wherein said laser is adapted to move from a first end of said enclosure to a second end of said enclosure on said rack for performing said laser surgery on any part of the subject.

5. The system of claim 4, wherein said surgical trays are mounted on the interior surface of said enclosure.

6. The system of claim 5, wherein said inert gas is nitrogen.

7. The system of claim 1, further comprising a vacuum pump to assist in removing oxygen from said enclosure.

8. A method for enclosing a subject on an operating table during a surgical procedure for removal of a suspected cancer, the subject being positioned on an upper surface of the operating table, comprising the steps of:
   a) placing a transparent enclosure having a lower lip extending completely around a periphery of the enclosure over the subject, and securing the enclosure to the operating table, the operating table having an upper planar portion extending to an outer edge thereof, using a gasket between the lower lip and the outer edge of the upper planar portion extending completely around the enclosure, and clamps engaging the lower lip and the outer edge of the upper planar portion for sealing the enclosure on the operating table and completely enclosing the subject;
   b) disposing a plurality of surgical gloves on an interior surface of the enclosure, medical personnel inserting their hands into the surgical gloves so that the medical personnel can perform the surgical procedure on the subject within the enclosure while the medical personnel are positioned outside of the enclosure, and using junction receptacles disposed in a wall of said enclosure for administering medicines when needed;
   c) adapting a source of oxygen to supply oxygen directly to the subject through a face mask during the surgical procedure;
   d) adapting a source of inert gas absent may oxygen to supply the inert gas to an interior of the enclosure outside of the breathing mask;
   e) purging oxygen from the enclosure using the inert gas in sufficient amounts, as determined by an oxygen analyzer within the enclosure, to obtain and maintain an atmosphere of the inert gas under positive pressure containing oxygen with the oxygen level being brought to less than 1% within the enclosure during the surgical procedure in order to eliminate, any possibility of spread of any cancer cells;
   f) the oxygen analyzer monitoring a level of oxygen on the interior of the enclosure so that the level of oxygen is less than 1%; and g) movably mounting a laser on a rack fixed in the interior of the enclosure to perform the surgical procedure on the subject in said atmosphere of less than 1% oxygen.

9. The method of claim 8, further comprising a step of providing a plurality of access ports in the enclosure to permit articles to be passed from the outside of the enclosure to the interior of the enclosure.

10. The method of claim 9, wherein the plurality of surgical gloves are adapted to form an airtight seal between the enclosure and the plurality of surgical gloves.

11. The method of claim 10, wherein the laser is adapted to move from a first end of the enclosure to a second end of the enclosure for performing laser surgery on any part of the subject.

12. The method of claim 11, further comprising a step of providing a surgical tray on the interior of the enclosure, the surgical tray containing articles therein.

13. The method of claim 12, further comprising mounting the surgical tray on the interior surface of the enclosure.

14. The method of claim 13, wherein the inert gas is nitrogen.

15. The method of claim 8, further comprising a step of providing a vacuum pump to assist in removing oxygen from the enclosure.

* * * * *